United States Patent
Amanullah et al.

(10) Patent No.: US 9,739,694 B2
(45) Date of Patent: Aug. 22, 2017

(54) METHOD AND APPARATUS FOR TESTING GEL-BASED LOST CIRCULATION MATERIALS

(71) Applicant: Saudi Arabian Oil Company, Dhahran (SA)

(72) Inventors: Md Amanullah, Dhahran (SA); Turki Thuwaini Mohammed Alsubaie, Dhahran (SA)

(73) Assignee: SAUDI ARABIAN OIL COMPANY (SA)

( * ) Notice: Subject to any disclaimer, the term of this patent is extended or adjusted under 35 U.S.C. 154(b) by 173 days.

(21) Appl. No.: 14/837,741

(22) Filed: Aug. 27, 2015

(65) Prior Publication Data

US 2016/0061701 A1 Mar. 3, 2016

Related U.S. Application Data

(60) Provisional application No. 62/042,945, filed on Aug. 28, 2014.

(51) Int. Cl.
  *G01N 3/08* (2006.01)
  *G01N 3/00* (2006.01)
  (Continued)

(52) U.S. Cl.
  CPC ............... *G01N 3/08* (2013.01); *C09K 8/03* (2013.01); *E21B 21/003* (2013.01); *G01N 3/12* (2013.01);
  (Continued)

(58) Field of Classification Search
  None
  See application file for complete search history.

(56) References Cited

U.S. PATENT DOCUMENTS

| 4,411,160 A | 10/1983 | Lutenegger et al. |
| 4,748,849 A | 6/1988 | Jamison et al. |

(Continued)

FOREIGN PATENT DOCUMENTS

| WO | 0224771 A2 | 3/2002 |
| WO | 2014197417 A1 | 12/2014 |

OTHER PUBLICATIONS

PCT International Search Report and the Written Opinion of the International Searching Authority dated Nov. 17, 2015; International Application No. PCT/US2015/047130; International Filing Date: Aug. 27, 2015.

(Continued)

*Primary Examiner* — Peter Macchiarolo
*Assistant Examiner* — Jermaine Jenkins
(74) *Attorney, Agent, or Firm* — Bracewell LLP; Constance Gall Rhebergen

(57) ABSTRACT

A compression test rig apparatus for determining a mechanical characterization of a gel-based LCM test sample comprising an LCM test cell configured to contain the gel-based LCM test sample, the LCM test cell comprising a cylinder wall defining a cell space volume configured to hold the gel-based LCM test sample, and a floor defining an extrusion hole configured to extrude the gel-based LCM test sample to create an extruded gel; an extruded gel collector configured to receive the extruded gel from the extrusion hole as an extruded gel volume; a perforated disc comprising perforations, wherein the perforated disc is configured to allow the gel-based LCM test sample to pass through the perforations; and a flat foot disc piston in flush contact with the cylinder wall, the flat foot disc piston configured to compress the gel-based LCM test sample at a displacement speed to produce compression data.

21 Claims, 10 Drawing Sheets

(51) Int. Cl.
- *G01B 5/30* (2006.01)
- *G01B 7/16* (2006.01)
- *E21B 21/00* (2006.01)
- *G01N 3/12* (2006.01)
- *G01N 11/04* (2006.01)
- *G01N 33/28* (2006.01)
- *C09K 8/03* (2006.01)
- *G01N 11/00* (2006.01)

(52) U.S. Cl.
CPC ......... *G01N 11/04* (2013.01); *G01N 33/2823* (2013.01); *G01N 2011/0033* (2013.01)

(56) References Cited

U.S. PATENT DOCUMENTS

| | | | |
|---|---|---|---|
| 5,197,324 A | 3/1993 | Keys | |
| 5,372,641 A | 12/1994 | Carpenter | |
| 6,145,591 A | 11/2000 | Boncan et al. | |
| 6,269,684 B1 | 8/2001 | Maki, Jr. et al. | |
| 6,530,437 B2* | 3/2003 | Maurer | E21B 21/08 166/310 |
| 7,297,208 B2 | 11/2007 | Caveny et al. | |
| 7,751,980 B2 | 7/2010 | Yan et al. | |
| 8,132,623 B2 | 3/2012 | Allin et al. | |
| 8,186,456 B2* | 5/2012 | Tibbitts | E21B 7/18 166/55.8 |
| 8,573,048 B2 | 11/2013 | Slater et al. | |
| 8,822,388 B2* | 9/2014 | Burns | C09K 8/5083 507/219 |
| 8,863,567 B2 | 10/2014 | Jappy et al. | |
| 2005/0167159 A1 | 8/2005 | Bailey et al. | |
| 2011/0214870 A1 | 9/2011 | Shaarpour | |
| 2011/0290012 A1 | 12/2011 | Jappy et al. | |
| 2013/0192358 A1 | 8/2013 | Murphy et al. | |
| 2014/0102188 A1* | 4/2014 | Murphy | G01N 33/2823 73/152.05 |
| 2014/0182369 A1 | 7/2014 | Blue et al. | |
| 2014/0306156 A1 | 10/2014 | Tian et al. | |
| 2014/0353043 A1 | 12/2014 | Amanullah et al. | |

OTHER PUBLICATIONS

Ay, A., et al.; An Experimental Study of Silicate-Polymer Gel Systems to Seal Shallow Water Flow and Lost Circulation Zones in Top Hole Drilling, Journal of Petroleum Science and Engineering; Sep. 28, 2014; pp. 690-699; vol. 122; Elsevier E.V.

Bendow, J. J., et al.; The Flow of Pastes Through Dies of Complicated Geometry; Powder Technology; Mar. 1, 1991; pp. 393-401; vol. 65, No. 1-3; Elsevier E.V.

El Hassan, H. I., et al.; Using a Novel Fiber Cement System to Control Lost Circulation; Case Histories from the Middle East and the Far East; SPE/IADC Middle East Drilling Technology Conference and Exhibition; Oct. 20-22, 2003; pp. 273-279.

* cited by examiner

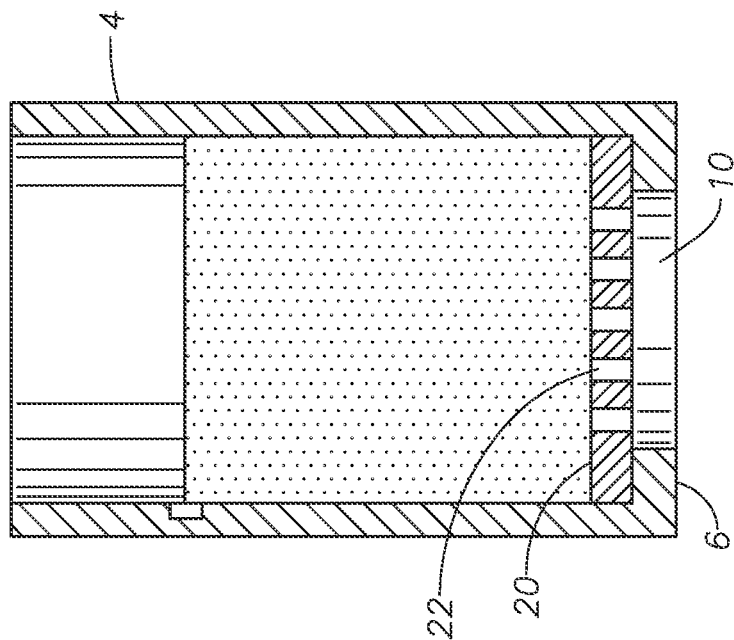
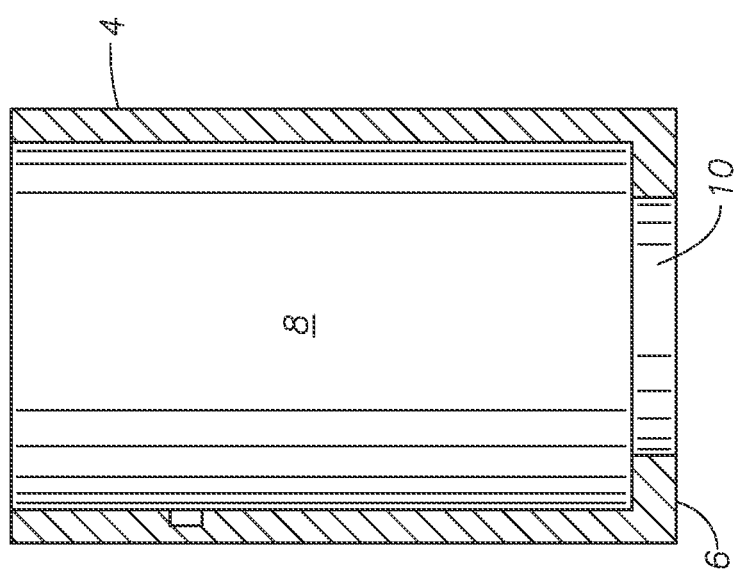
FIG. 1D
FIG. 1C

METHOD AND APPARATUS FOR TESTING GEL-BASED LOST CIRCULATION MATERIALS

RELATED APPLICATION

This application claims priority from U.S. Provisional Patent Application No. 62/042,945 filed on Aug. 28, 2014. For purposes of United States patent practice, this application incorporates the contents of the Provisional patent application by reference in its entirety. This application further relates to, claims priority to and the benefit of, and incorporates by reference U.S. Non-Provisional patent application Ser. No. 14/294,378 filed on Jun. 3, 2014.

BACKGROUND

Technical Field

Embodiments generally relate to methods to test lost circulation materials. More specifically, embodiments relate to methods and apparatus to test and characterize gel based lost control materials.

Description of the Related Art

Lost circulation is one of the frequent challenges encountered during drilling operations. Lost circulation, which can be encountered during any stage of operations, occurs when a drilling fluid (also known as a drilling "mud") is pumped into a well and either returns partially or does not return at all to the surface. While some fluid loss is expected, fluid loss beyond acceptable norms is not desirable from a technical, an economical, or an environmental point of view. About 75% of the wells drilled per year encounter lost circulation problems to some extent. Lost circulation is associated with problems of well control, borehole instability, pipe sticking, unsuccessful production tests, poor hydrocarbon production after well completion, and formation damage due to plugging of pores and pore throats by mud particles. In extreme cases, lost circulation problems may force abandonment of a well. In addition, delays in controlling lost circulation can lead to highly complex problems, including the failure to control the lost circulation in any meaningful way.

Billions of dollars are lost per year due to lost circulation in drilling operations. Lost dollars are due to losses of drilling fluids, losses of production, and the costs of lost circulation materials (LCMs) used in combating lost circulation.

Lost circulation can cause environmental problems if drilling muds or LCMs interact with the environment surrounding the reservoir. Conventional LCMs pose a risk to sensitive environments, such as marine environments because they are not biodegradable and can be toxic to marine life. Public awareness of drilling operations, including the drilling fluids used, has contributed to demands from environmental regulatory bodies to develop biodegradable and virtually non-toxic LCMs.

Lost circulation can be categorized as seepage type, moderate type, severe type, and total loss, referring to the amount of fluid or mud lost. The extent of the fluid loss and the ability to control the lost circulation with an LCM depends on the type of formation in which the lost circulation occurs. Formations with low permeability zones, that is, those with microscopic cracks and fissures, usually have seepage type lost circulation. Seepage type lost circulation experiences a loss of less than 10 barrels/hour (bbl/hr) for water based drilling muds, or about 10 bbl/hr for oil based drilling muds. Formations with narrow fracture sizes and lower fracture density usually trigger a moderate loss of drilling mud. A moderate type lost circulation experiences a loss at a rate in the range of about 10 bbl/hr to about 100 bbl/hr. Formations with high permeability zones, such as super-K formations, highly fractured formations with large fracture sizes and high fracture density, often experience very high mud loss with a drastic increase in total mud and mud management costs. A severe type lost circulation experiences losses of greater than about 100 bbl/hr. Formations with inter-connected vugular and cavernous zones or formations with induced inter-vugular connection often cause massive loss of drilling mud with no return of circulation. It is possible for one wellbore to experience all of these zones.

Other formations may experience lost circulation if an improper mud weight is used while drilling. Such formations include narrow mud weight window, low fracture gradient, depleted reservoir pressure, formations with soluble minerals such as halite, evaporate, and anhydrite.

In general, seepage type and moderate type losses occur more frequently than severe type lost circulation. In the Saudi Arabian fields, however, the formations encountered while drilling reservoir and non-reservoir sections have unique depositional histories and matrix characteristics that make the super-K, fractured, vuggy, cavernous, faulted characteristics of the carbonate rock formations prone to moderate to massive loss of drilling fluid. Some of the losses are so massive that hundreds of barrels of mud are lost in an hour with no return of fluid to the mud return line, as the rate of loss usually exceeds the rate of replacement of drilling mud. Thus, even though the frequency of severe lost circulation is less than seepage or moderate lost circulation, severe lost circulation has a significant economic impact on drilling operations.

LCMs are used to mitigate the lost circulation by blocking the path of the fluid. The type of LCM used in a loss circulation situation depends on the extent of lost circulation and the type of formation. Conventional LCMs, currently available in the industry, include particulates, flaky materials, granular materials, and gel LCMs including cross-linked gels, cross-linked polyacrylamides, polyacrylates, super absorbing polymers (SAP), or a combination of the above. Conventional gel LCMs typically contain one or more polymers, one or more monomers, one or more cross-linkers, including chemical cross-linkers, a cross-linking initiator, and a fluid phase, such as water or oil. Some formulations may include particles.

For zones experiencing seepage type to moderate type lost circulation, conventional LCMs that include particulates, flakes, gels or a combination of such are often effective in controlling the loss zones. Polymeric and gel LCMs are also commonly used to control moderate to severe loss of circulation, due to their ability to swell, gel, crosslink, expand, or a combination of such. For example, SAPs expand many times in volume in the presence of water. The swelling, gelling, crosslinking, or expansion of the LCMs helps to stop the loss of drilling mud by plugging the fractures or the vugs. However, many high permeability zones experience limited success in attempts to control a lost circulation event, even with the use of conventional non-gel and gel LCMs. For formations with massive loss of drilling mud, current chemical methods of loss control rarely work.

Poor control in a lost circulation zone is often due to the LCM itself. The efficacy of a gel LCM depends in large part on the fracture dimensions, but also on the gel characteristics. A soft gel can control seepage type loss zones, but because soft gels cannot resist the stresses caused by fluids being pumped into the formation, a soft gel LCM will continue to move through the fractures and channels of moderate to severe loss zones without creating an effective flow barrier. If the gel LCM cannot seal the lost circulation zone effectively, it may not bring the mud loss below the maximum allowable limit. In some cases, the gel may not be capable of solidifying at all. Tests indicate that especially in vugular formations, conventional gel LCMs perform poorly.

Conventional gel LCMs usually have poor thermal stability, chemical stability, and low value gel characteristics and low tolerance for salt, making them unsuitable for some environments, for example, marine environments, and thus have limited capacity in controlling loss of circulation, especially in highly fractured and cavernous formations.

In addition, the formulations of conventional gel LCMs require special preparation and handling. Special preparations can include the order in which the components are mixed, mixing techniques, or the need for specialized mixing units. If the formulation guidelines are not followed precisely, the conventional gel LCM may not obtain homogeneous gel characteristics. Careful handling implies the placement and pumping of the LCM into the formation. Conventional gel LCMs require precise placement in the formation due to the reaction kinetics of the polymers and cross-linkers. Proper placement ensures that the materials reach the proper gel characteristics at the target location. Proper placement in turn depends on the pumping schedule and the pumping units, which often must be highly specialized. In addition, drilling operations are usually stopped until the lost circulation zone is sealed and fluid losses to the formation are reduced to an acceptable level.

The requirements for preparation and placement mean that significant time can lapse between reaching lost circulation and beginning control measures with conventional gel-based LCMs. At a minimum, the time lapse translates to a substantial volume loss of drilling fluid. At worst, the extended preparation time may aggravate the problem, turning a manageable lost circulation problem into a situation in which lost circulation control is not possible and the entire well must be shut-down.

The industry needs methods to characterize the conventional gel LCMs, so that deployment of the proper gel LCM can occur to minimize downtime and maximize recovery.

SUMMARY

Embodiments generally relate to methods to test lost circulation materials. More specifically, embodiments relate to methods and apparatus to test and characterize gel based lost control materials.

In one aspect, a compression test rig apparatus for determining a mechanical characterization of a gel-based LCM test sample is provided. The compression test rig apparatus includes an LCM test cell, the LCM test cell configured to contain the gel-based LCM test sample, the LCM test cell includes a cylinder wall, the cylinder wall defining a cell space volume, wherein the cell space volume is configured to hold the gel-based LCM test sample, and a floor, the floor being physically connected to the cylinder wall, the floor defining an extrusion hole, the extrusion hole having an extrusion hole diameter, the extrusion hole configured to extrude the gel-based LCM test sample to create an extruded gel. The compression test rig apparatus further includes an extruded gel collector, the extruded gel collector being proximate to the floor of the LCM test cell, the extruded gel collector configured to receive the extruded gel from the extrusion hole as an extruded gel volume, a perforated disc, the perforated disc being in contact with the floor of the LCM test cell and flush with the cylinder wall, the perforated disc including perforations, wherein the perforated disc is configured to allow the gel-based LCM test sample to pass through the perforations, and a flat foot disc piston, the flat foot disc piston in flush contact with the cylinder wall of the LCM test cell, the flat foot disc piston configured to compress the gel-based LCM test sample contained in the cell space volume at a displacement speed to produce compression data.

In certain embodiments, the compression test rig apparatus further includes an acquisition system, the acquisition system in electronic communication with the LCM test cell, the acquisition system configured to record the compression data, the acquisition system further configured to display the compression data. In certain embodiments, the compression test rig apparatus further includes a piston rod mechanically connected to the flat foot disc piston, configured to move the flat foot disc piston between a fill level and a compressed level, a load cell carrier arm mechanically connected to the piston rod, the load cell carrier arm configured to apply a load to the piston rod, wherein the load is operable to be variable in order to maintain a constant displacement speed, a load cell, the load cell mechanically connected to the load carrier arm, the load cell configured to measure a measured reactive force of the gel-based LCM test sample, the load cell further configured to convert the measured reactive force into an electrical signal, wherein the electrical signal is recorded by the acquisition system, wherein the measured reactive force is produced in response to being compressed by the flat foot disc piston, and a normal stress applicator, the normal stress applicator mechanically connected to the load cell carrier arm, the normal stress applicator configured to generate the load. In certain embodiments, the perforations include a central perforation, the central perforation being in the center of the perforated disc, the central perforation having a central perforation diameter, and a plurality of peripheral perforations, the plurality of peripheral perforations arranged in a ring around the central perforation to form a perforation ring, the perforation ring having a perforation ring diameter, the plurality of peripheral perforations having a peripheral perforation diameter. In certain embodiments, the extrusion hole diameter is 3.3 centimeters (cm). In certain embodiments, the central perforation diameter is 3 millimeters (mm). In certain embodiments, the peripheral perforation diameter is 3 mm. In certain embodiments, the perforation ring diameter is 2.6 cm. In certain embodiments, the mechanical characterization is selected from the group consisting of yield strength, gel stiffness modulus, and combinations thereof. In certain embodiments, the displacement speed is 1 millimeter/second (mm/sec). In certain embodiments, the compression data is selected from the group consisting of time, the extruded gel volume, the load, the measured reactive force, the fill level, the compressed level, and combinations thereof.

In a second aspect, a method for determining a mechanical characterization of a gel-based LCM using a compression test rig is provided. the method includes the steps of placing a gel-based LCM sample volume in a cell space volume of a LCM test cell of the compression test rig, the compression test rig includes an LCM test cell, the LCM test cell configured to contain the gel-based LCM test sample, the LCM test cell includes a cylinder wall, the cylinder wall defining the cell space volume, wherein the cell space volume is configured to contain the gel-based LCM test sample, and a floor, the floor physically connected to the cylinder wall, the floor defining an extrusion hole, the extrusion hole having an extrusion hole diameter, the extrusion hole configured to extrude the gel-based LCM test sample to create an extruded gel, wherein the gel-based LCM sample volume fills the cell space volume to a fill level, an extruded gel collector, the extruded gel collector proximate to the floor of the LCM test cell, the extruded gel collector configured to receive the extruded gel from the extrusion hole as an extruded gel volume, a perforated disc, the perforated disc in contact with the floor of the LCM test cell and flush with the cylinder wall, the perforated disc including perforations, wherein the perforated disc is configured to allow the gel-based LCM test sample to pass through the perforations, and a flat foot disc piston, the flat foot disc piston in flush contact with the cylinder wall of the LCM test cell, the flat foot disc piston configured to compress the gel-based LCM test sample contained in the cell space volume at a displacement speed to produce compression data. The method further includes the steps of placing the flat foot disc piston at the fill level in contact with the gel-based sample volume, applying a load to the flat foot disc piston to move the flat foot disc toward the floor of the LCM test cell at a displacement speed, wherein the flat foot disc compresses the gel-based LCM test sample contained in the cell space volume, wherein the gel-based LCM test sample is compressed to a compressed level, wherein a measured reactive force is produced in response to being compressed by the flat foot disc piston, and measuring compression data with an acquisition system, the acquisition system in electronic communication with the LCM test cell, the acquisition system configured to record the compression data, the acquisition system further configured to display the compression data.

In certain embodiments, the method further includes the steps of generating the load in a normal stress applicator, the normal stress applicator mechanically connected to a load cell carrier arm, the normal stress applicator configured to generate the load, wherein the load is operable to be variable in order to maintain a constant displacement speed, moving the load cell carrier arm, the load cell carrier arm mechanically connected to a piston rod, the load cell carrier arm configured to apply the load to the piston rod, the load cell carrier arm including a load cell, the load cell mechanically connected to the load carrier arm cell, the load cell configured to measure a measured reactive force of the gel-based LCM test sample, the load cell further configured to convert the measured reactive force into an electrical signal, wherein the electrical signal is recorded by the acquisition system, wherein the measured reactive force is produced in response to being compressed by the flat foot disc piston, and moving the piston rod, the piston road mechanically connected to the flat foot disc piston, the piston rod is configured to move the flat foot disc piston between the fill level and the compressed level. In certain embodiments, the perforations include a central perforation, the central perforation in the center of the perforated disc, the central perforation having a central perforation diameter, and a plurality of peripheral perforations, the plurality of peripheral perforations arranged in a ring around the central perforation to form a perforation ring, the perforation ring having a perforation ring diameter, the plurality of peripheral perforations having a peripheral perforation diameter. In certain embodiments, the extrusion hole diameter is 3.3 cm. In certain embodiments, the central perforation diameter is 3 mm. In certain embodiments, the peripheral perforation diameter is 3 mm. In certain embodiments, the perforation ring diameter is 2.6 cm. In certain embodiments, the mechanical characterization is selected from the group consisting of yield strength, gel stiffness modulus, and combinations thereof. In certain embodiments, the displacement speed is 1 mm/sec. In certain embodiments, the compression data is selected from the group consisting of time, the extruded gel volume, the load, the measured reactive force, the fill level, the compressed level, and combinations thereof.

BRIEF DESCRIPTION OF THE DRAWINGS

These and other features, aspects, and advantages will become better understood with regard to the following descriptions, claims, and accompanying drawings. It is to be noted, however, that the drawings illustrate only several embodiments and are therefore not to be considered limiting of the inventive scope as it can admit to other equally effective embodiments.

FIG. 1c is a sectional elevation view of an embodiment of an LCM test cell.

FIG. 1d is a sectional elevation view of an embodiment of an LCM test cell with a perforated disc and an LCM test sample.

DETAILED DESCRIPTION OF THE INVENTION

Figure 1A:
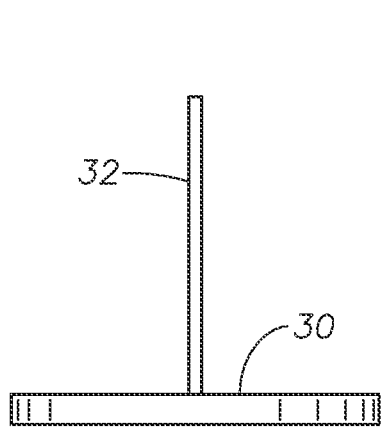
FIG. 1a is a plan view of an embodiment of a flat foot disc piston.

The scope of the present invention will now be described more fully with reference to the accompanying drawings, which illustrate embodiments of the invention. This invention may, however, be embodied in many different forms and should not be construed as limited to the illustrated embodiments set forth here. Rather, these embodiments are provided so that this disclosure will be thorough and complete, and will fully convey the scope of the invention to those skilled in the art. In both the drawings and the detailed description like numbers refer to like elements throughout.

Compression test rig apparatus 100 for determining a mechanical characterization of an LCM is provided. The LCM is any LCM for which an LCM test sample can be obtained. The LCM test sample can be a conventional LCM, a gel-based LCM, or a blend. The LCM test sample can be a commercially available LCM. In at least one embodiment, the LCM test sample is a gel-based LCM test sample. In at least one embodiment, the LCM test sample is created by mixing the LCM components to produce the LCM and then collecting a test sample.

The mechanical characterization of the LCM is a characteristic of the LCM that is indicative of the behavior of the LCM in different loss circulation zones, such as the ability of the LCM to gel, to resist flow, or to exhibit the ability to control loss of circulation. The scope of the present invention advantageously provides a method for determining the two mechanical characterizations developed by the inventor for use in characterizing gel-based LCMs: yield strength and gel stiffness modulus. The yield strength and the gel stiffness modulus are indicative of the extent to which the gel LCM resists flow when forces are applied. Yield strength is a measure of the strength of a material, it is the force required to initiate plastic deformation. The yield strength is a measure of the maximum reaction force generated by the gel matrix of the gel-based LCM under the compressive force before the initiation of flow of the gel-based LCM. The magnitude of this reaction force depends on the gel matrix bond, or network strength, and is a characteristic property of gel-based LCMs. The yield strength value of a gel-based LCM can be used in a comparative assessment of that gel-based LCM to other LCMs. The gel stiff modulus is a measure of the extent to which a material resists deformation in response to an applied load. Gel stiffness modulus is the extent to which a material resists deformation in response to an applied load, in other words it is a measure of the rigidity of the material. A high gel stiffness modulus and high yield strength indicate a gel that is resistant to deformation and that is therefore likely to solidify into a rigid gel. A gel with a low yield strength and low gel stiffness modulus is likely to form a soft gel system.

Compression test rig apparatus 100 include LCM test cell 2. LCM test cell 2 contains the LCM test sample during the compression test. LCM test cell 2 has cylinder wall 4 and floor 6. Floor 6 is connected to cylinder wall 4. In at least one embodiment, LCM test cell 2 is secured with adjustable screws. Floor 6 can be connected to cylinder wall 4 by any means capable of ensuring a seal between cylinder wall 4 and floor 6. Cylinder wall 4 and floor 6 create a rigid frame. Cylinder wall 4 and floor 6 can be made out of any material that resists deformation when subjected to the compression force of compression test rig apparatus 100. In at least one embodiment, LCM test cell 2 is bored from a solid block of material. Floor 6 includes extrusion hole 10. Extrusion hole 10 extends through the entire thickness of floor 6. Extrusion hole 10 has an extrusion hole diameter. The extrusion hole diameter is between about 2 cm and 4 cm. In at least one embodiment, the extrusion hole diameter is about 3.3 cm.

Perforated disc 20 lies on floor 6 in contact with floor 6 and flush with cylinder wall 4. As used herein, flush means that an object fits tightly against another object such that there are no gaps between the two objects. Perforated disc 20 fits tightly against cylinder wall 4 to prevent peripheral escape of the LCM test sample during the compression test, that is to prevent the LCM test sample from leaking around the sides of perforated disc 20. Perforated disc 20 includes perforations 22.

Figure 1B:
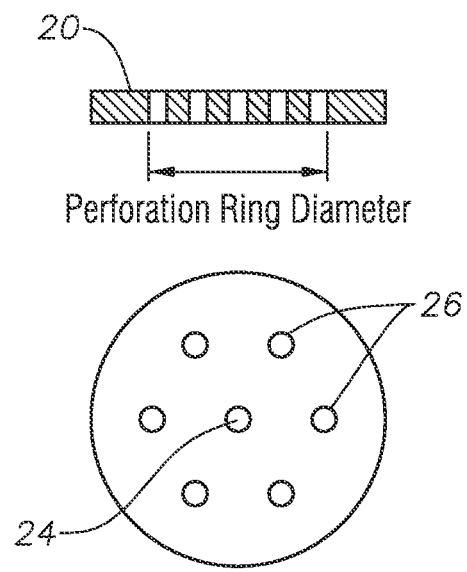
FIG. 1b is a sectional elevation view and a top plan view of an embodiment of a perforated disc.
Figure 2:
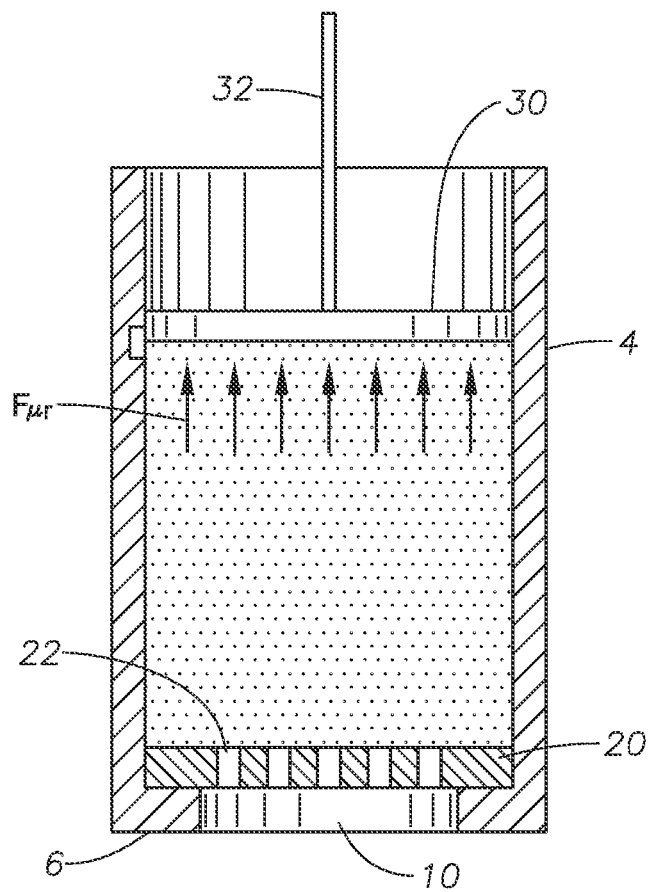
FIG. 2 is a sectional view of an embodiment of an LCM test cell showing the upward reactive forces when flat foot disc piston is placed on top of the LCM test sample.
Figure 1E:
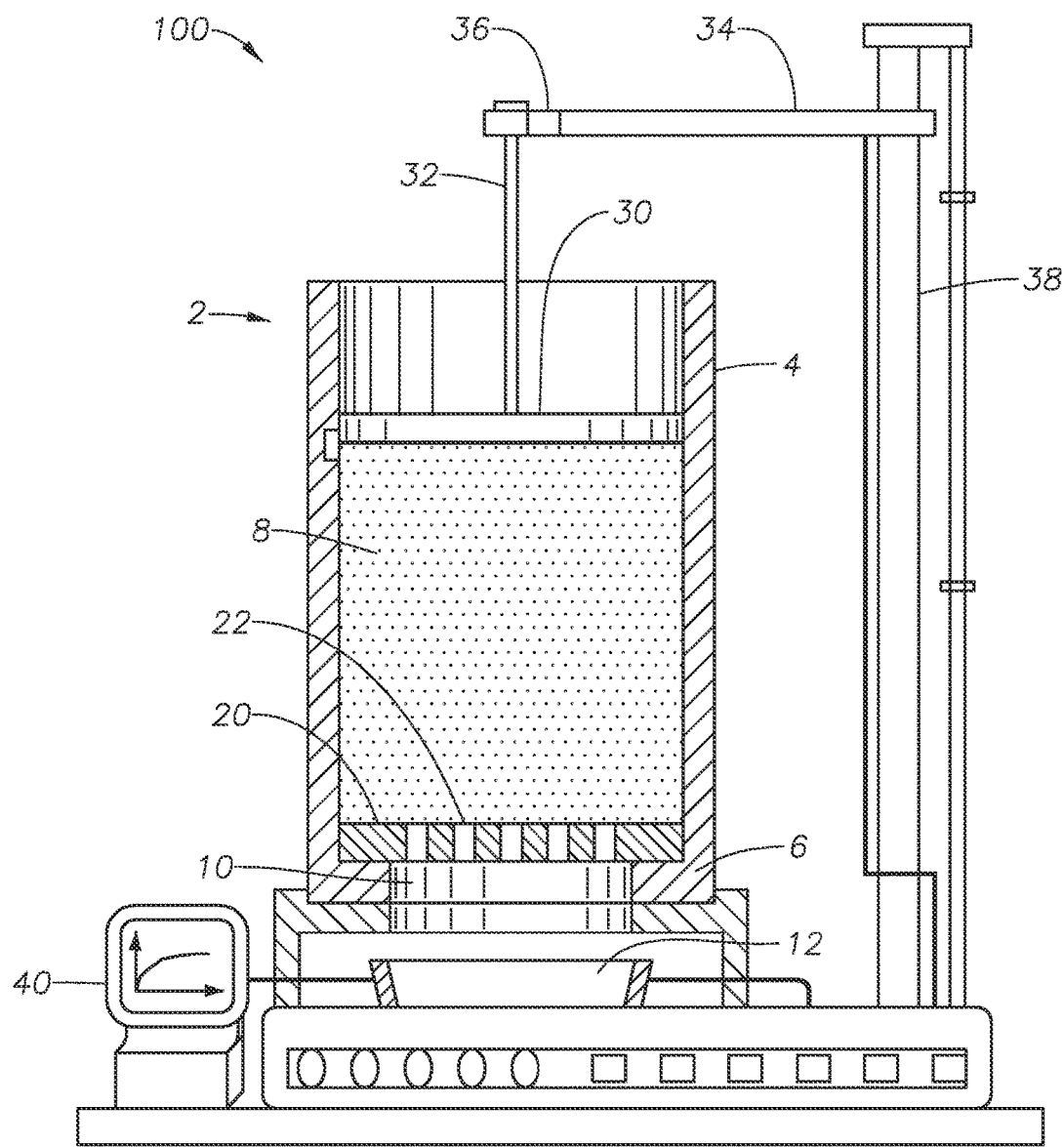
FIG. 1e is a sectional view of an embodiment of a compression test rig apparatus.

Perforations 22 extend through the thickness of perforated disc 20. Perforated disc 20 with perforations 22 simulates a loss zone. The number, diameter, and configuration of perforations 22 is selected to simulate a type of loss zone such as moderate or severe loss zone. In at least one embodiment, perforations 22 includes central perforation 24 and peripheral perforations 26, as shown in FIG. 1B. Central perforation 24 is located in the center of perforated disc 20. Central perforation 24 has a central perforation diameter. The central perforation diameter is between about 2 mm and about 5 mm. In at least one embodiment, the central perforation diameter is 3 mm.

Peripheral perforations 26 are arranged around central perforation 24 to form a perforation ring. In at least one embodiment, there are six peripheral perforations 26.

Peripheral perforations 26 each have a peripheral perforation diameter. The peripheral perforation diameter is between about 2 mm and about 5 mm. In at least one embodiment, the peripheral perforation diameter is 3 mm.

The perforation ring has a perforation ring diameter. The perforation ring diameter is smaller than the extrusion hole diameter. The perforation ring diameter is smaller than the extrusion hole diameter to eliminate or substantially eliminate cell base reaction during the compression test induced gel extrusion. The perforation ring diameter is between about 2 cm and about 5 cm. In at least one embodiment, the perforation ring diameter is 2.6 cm.

Cylinder wall 4 defines cell space volume 8. Cell space volume 8 is the interior volume of LCM test cell 2 bounded by cylinder wall 4 and perforated disc 20. Cell space volume 8 holds the LCM test sample during the compression test. The LCM test sample fills cell space volume 8 to a fill level. In at least one embodiment, the fill level is predetermined based on the dimensions of the LCM test cell 2. In at least one embodiment, the fill level is determined based on the size of the LCM test sample.

Extrusion hole 10 extrudes the LCM test sample to create an extruded gel. The extruded gel is collected in extruded gel collector 12.

Extruded gel collector 12 sits below and proximate to floor 6 to receive the extruded gel as an extruded gel volume. In at least one embodiment, extruded gel collector 12 is a pan. In at least one embodiment, extruded gel collector 12 sits on a scale (not shown) so that the weight of extruded gel volume can be ascertained.

Flat foot disc piston 30 fits within LCM test cell 2 flush with cylinder wall 4, the diameter of flat foot disc piston 30 being the same as the inner diameter of LCM test cell 2. Flat foot disc piston 30 sits flush with cylinder wall 4 to prevent back extrusion of the LCM test sample over the top of flat foot disc piston 30. The axis of flat foot disc piston 30 aligns with the axis of LCM test cell 2. Back extrusion of the LCM test sample would begin when the yield strength of the LCM test sample is reached during the compression test. At the start of the compression test, flat foot disc piston 30 rests on the LCM test sample at the fill level. Flat foot disc piston 30 is connected to piston rod 32. Piston rod 32 is connected to load cell carrier arm 34. Load cell carrier arm 34 applies a load to piston rod 32, causing piston rod 32 to move flat foot disc piston 30 between the fill level and a compressed level. The distance between the fill level and the compressed level is the displacement distance. The displacement distance is between about 20 mm and 60 mm, and alternately between about 30 mm and 50 mm. In at least one embodiment, the displacement distance is 40 mm. The flat foot disc piston 30 as it moves causes the LCM test sample in cell space volume 8 to compress generating compression data. Flat foot disc piston 30 moves at a displacement speed. The load applied by load cell carrier arm 34 is variable in order to maintain the displacement speed at a constant value. The displacement speed is between about 0.5 mm/sec and about 5 mm/sec. In at least one embodiment, the displacement speed is constant at 1 mm/sec. The load is generated by normal stress applicator 38, which is connected to load cell carrier arm 34. Load cell 36 connected to load carrier arm 34 measures a measured reactive force of the LCM test sample as the LCM test sample is being compressed due to the movement of flat foot disc piston 30. Load cell 36 converts the measured reactive force into an electrical signal and sends the electrical signal to acquisition system 40. Acquisition system 40 records the electrical signal from load cell 36 and records compression data from LCM test cell 2. The compression data recorded by acquisition system 40 includes length of time of the compression test, extruded gel volume, weight of extruded gel volume, the load, the measure reactive force, the fill level, the compressed level, and combinations thereof. Acquisition system 40 includes a means to display the compression data. A means to display the compression data includes a monitor. Acquisition system 40 includes a dedicated software driven operating system.

In at least one embodiment, compression test rig apparatus 100 includes a calibration platform. In at least one embodiment, compression test rig apparatus 100 includes position limiters. In at least one embodiment, compression test rig apparatus 100 includes an emergency stop button. In at least one embodiment, compression test rig apparatus 100 includes a control panel.

A method of using compression test rig apparatus 100 is herein provided. An LCM is produced by mixing the components. The LCM is allowed to cure for a cure time. The LCM test sample is prepared by collecting a volume of the LCM, wherein the volume will fill LCM test cell 2 to the fill level.

Perforated disc 20 selected so that it simulates the appropriate type of loss zone is selected. LCM test cell 2 is readied for the compression test by placing perforated disc 20 selected flush with floor 6 and placing extruded gel collector 12 under extrusion hole 10. The LCM test sample is placed in cell space volume 8 on top of perforated disc 20 up to the fill level. Flat foot disc piston 30 is set on top of the LCM test sample.

Normal stress applicator 38 generates the load which is transmitted through load cell carrier arm 34 and piston rod 32 to move flat foot disc piston 30 at the displacement speed during a pre-test phase and a test phase of the compression test. In at least one embodiment, the displacement speed is constant at 1 mm/sec. Flat foot disc piston 30 continues to compress the LCM test sample until the measured reactive force is reached and the LCM test sample is extruded from extrusion hole 10 through perforations 22. When extrusion flow is initiated, the compression test enters the post-test phase and flat foot disc piston 30 is returned to its original position at the fill level at a retraction speed. The refraction speed is at a constant rate. The constant refraction speed is between about 1 mm/sec and about 20 mm/sec, alternately between about 5 mm/sec and 15 mm/sec. In at least one embodiment, the retraction speed is constant at 10 mm/sec. During the test phase, acquisition system 40 records the load as a function of displacement distance. In at least one embodiment, acquisition system 40 displayed the compression data during the compression test.

The recorded load and displacement distance data is used to generate a load versus displacement curve. The load-displacement curve is used to determine the yield strength and the gel stiffness modulus.

The compression test takes advantage of the theory that a LCM test sample under a compressive force applied at constant displacement speed at the gel top develops an upward resistance force in response that is proportional to the compressive force. The upward resistance force resists the initiation of extrusion flow and continues until compressive force exceeds the yield strength value, causing the upward resistance force to fail. When the upward resistance force fails, the LCM test sample is extruded through perforations 22 that simulate the loss zone. Mathematically, the upward resistance force arising due to the compressive force applied on the gel top is expressed by the following equation:

$$F_{ur} = \int_0^h A\sigma_{ur}(h)dh$$

where,
$F_{ur}$ is the total upward resistance force,
A is the area of flat foot disc piston 30,
$\sigma_{ur}$ is the reactive stress, and
h is the displacement distance.

Yield Strength Determination

As stated above, the yield strength is the maximum reaction force generated by the gel matrix under the action of the compressive force before the initiation of flow of a gel-based LCM. On the load-displacement curve, the first peak, marked as YS on FIG. 3, indicates the initiation of extrusion flow of the LCM test sample, and, thus, the yield strength of the LCM test sample corresponds to the first peak of the load-displacement curve generated for that LCM test sample. The yield strength is a measure of force.

Gel Stiffness Modulus Determination

Figure 3:
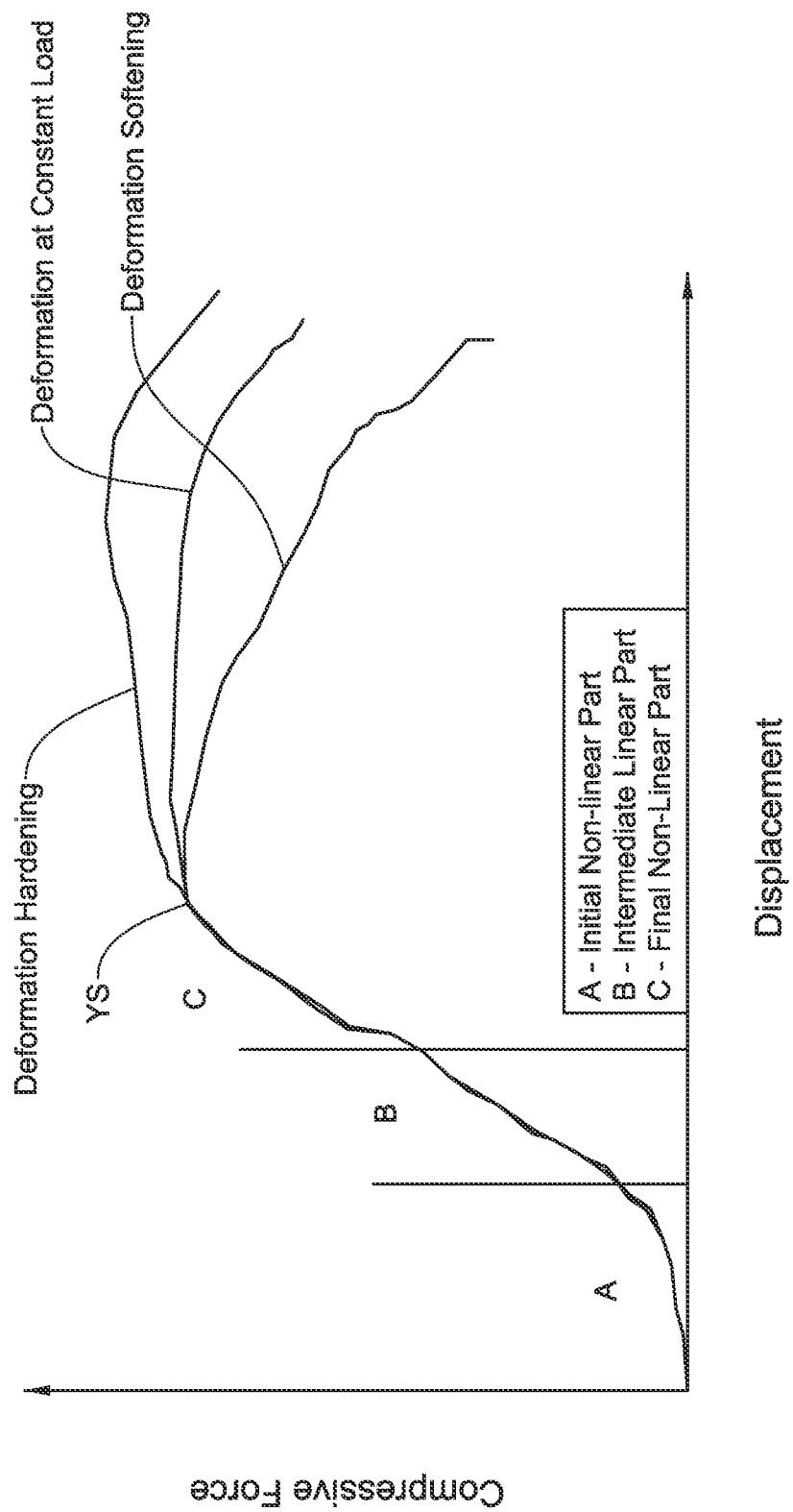
FIG. 3 is a representation of a graph of a displacement versus compressive force produced from compression data.
Figure 4:
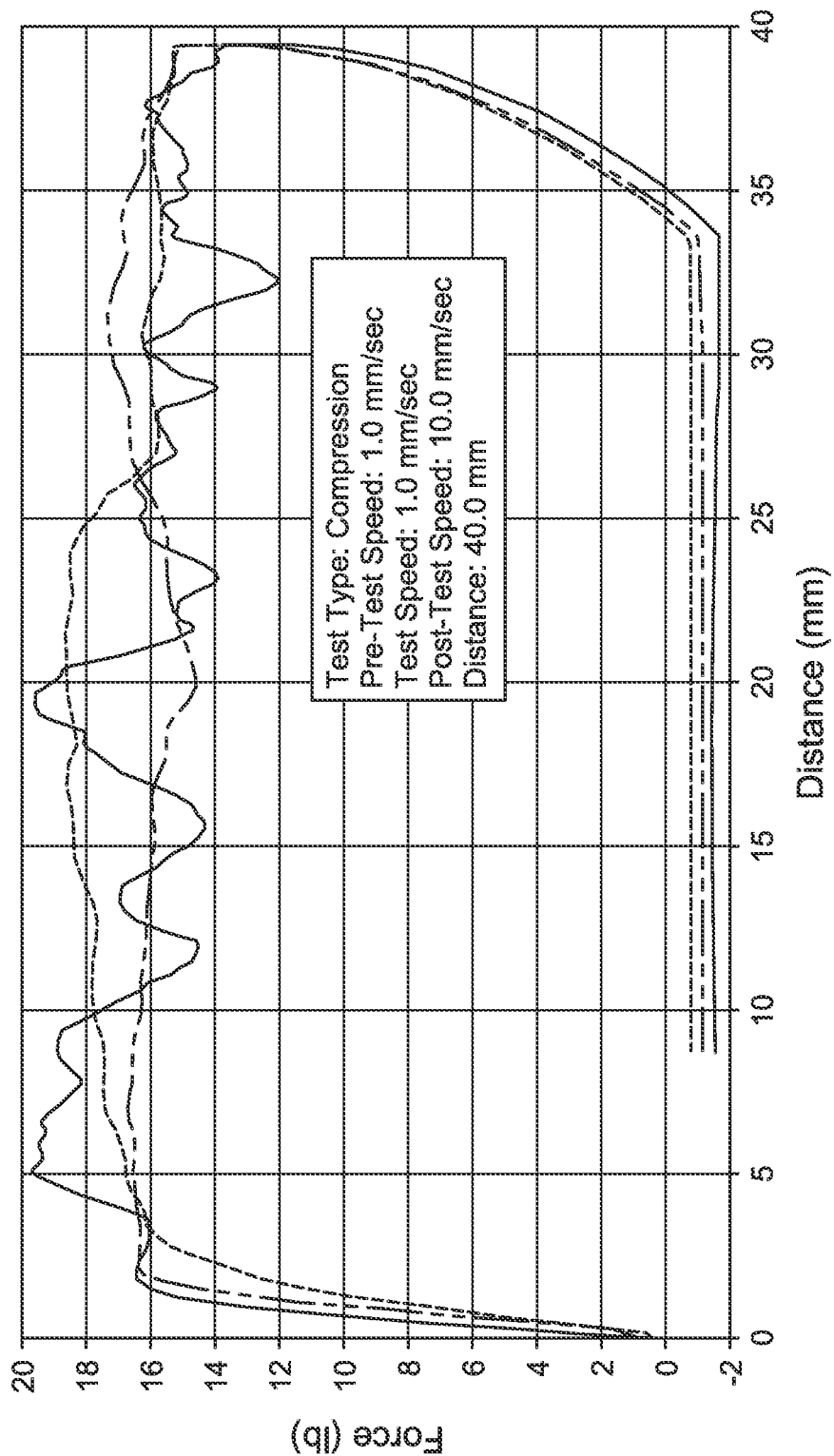
FIG. 4 is a graphic representation of the load-displacement curve generated from the compression data collected during the compression test of sample 1.
Figure 5:
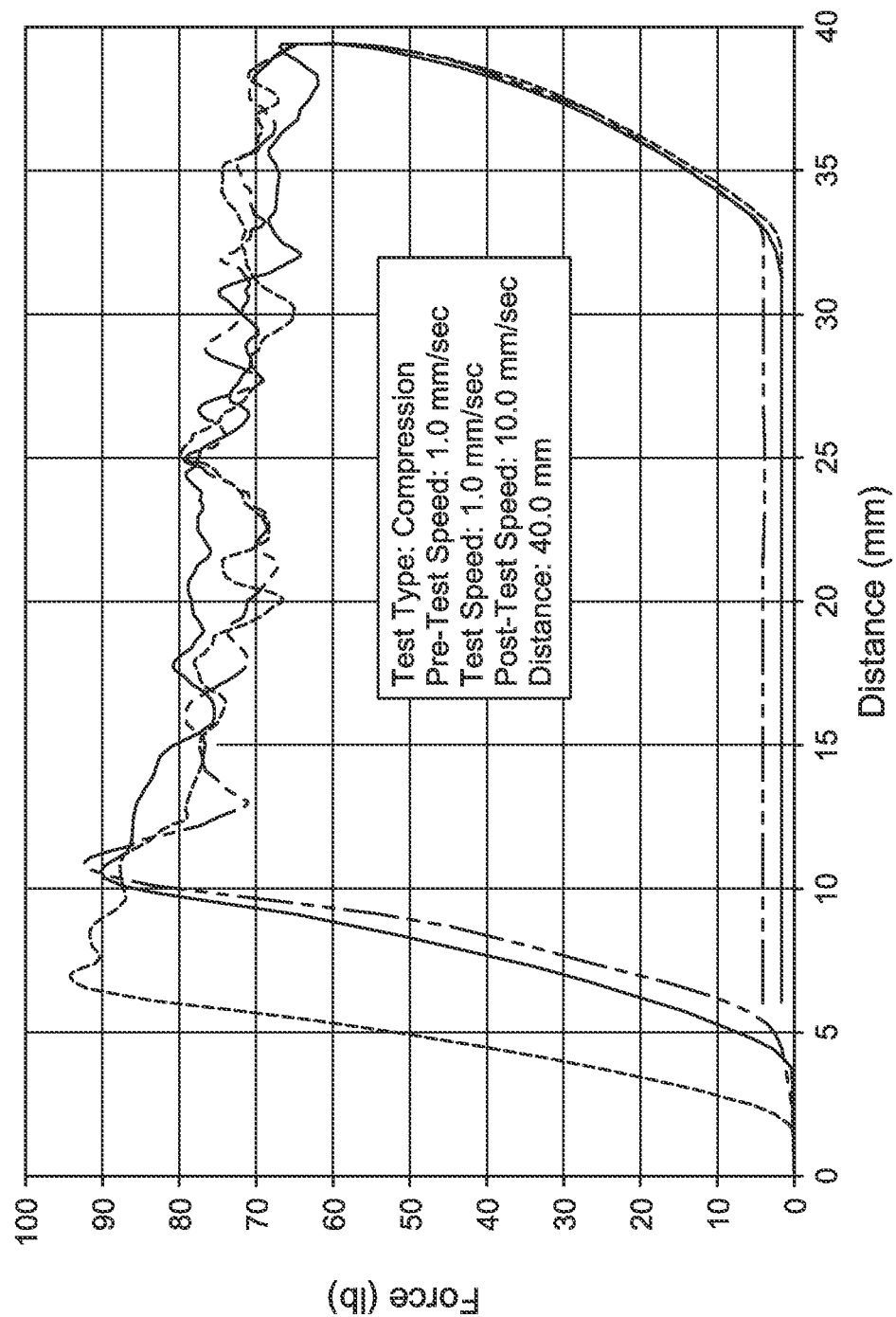
FIG. 5 is a graphic representation of the load-displacement curve generated from the compression data collected during the compression test of sample 2.
Figure 6:
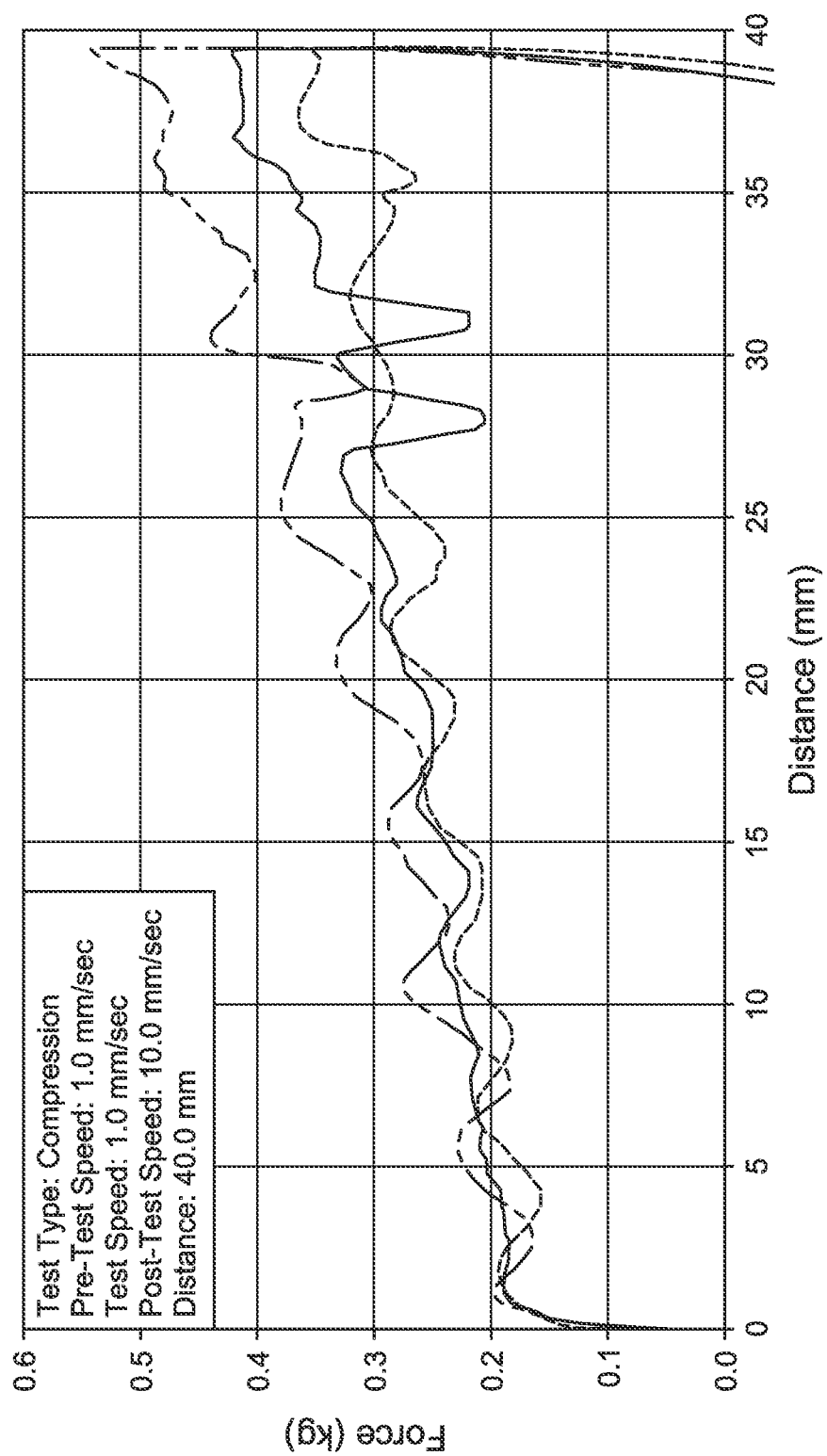
FIG. 6 is a graphic representation of the load-displacement curve generated from the compression data collected during the compression test of sample 3.
Figure 7:
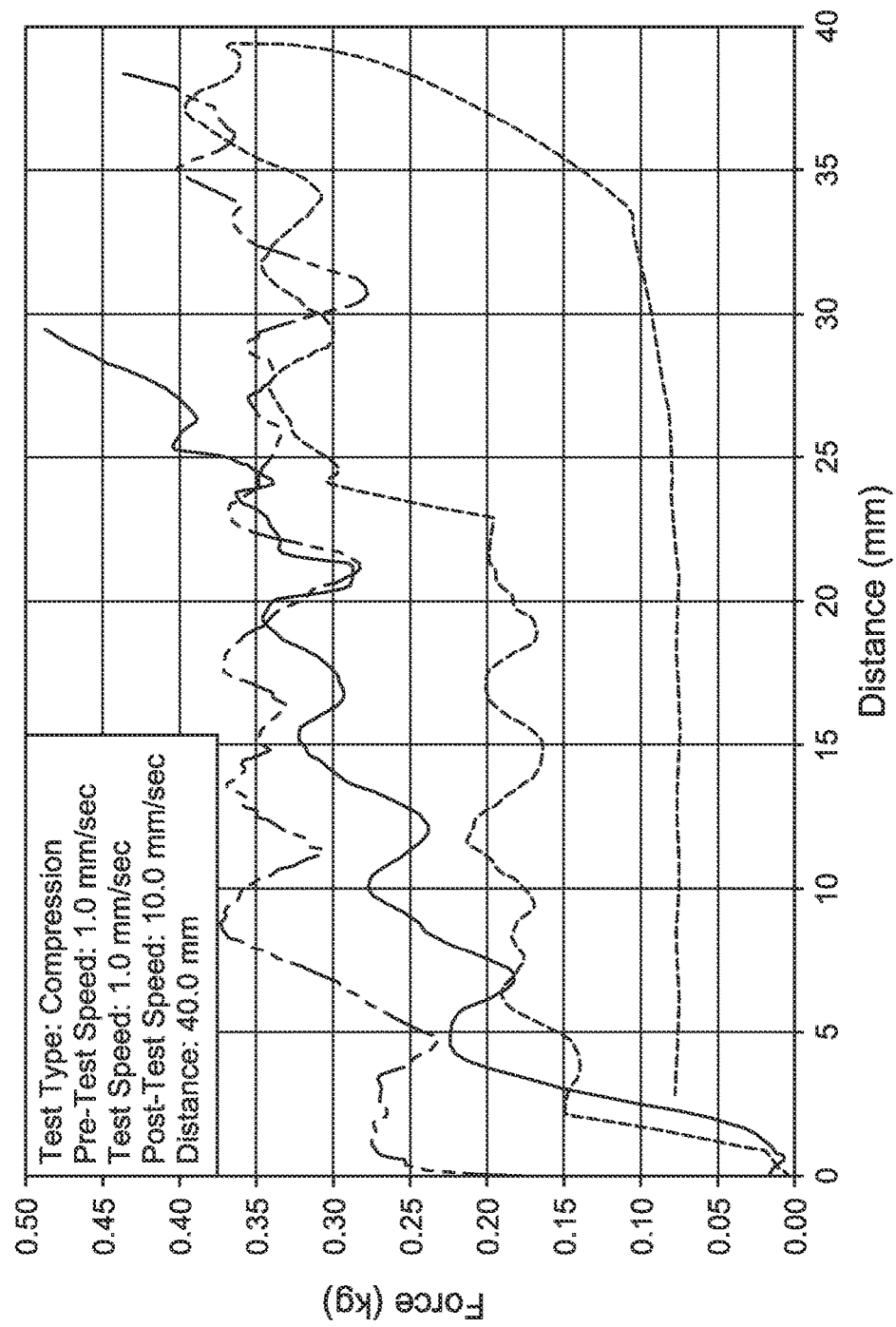
FIG. 7 is a graphic representation of the load-displacement curve generated from the compression data collected during the compression test of sample 4.
Figure 8:
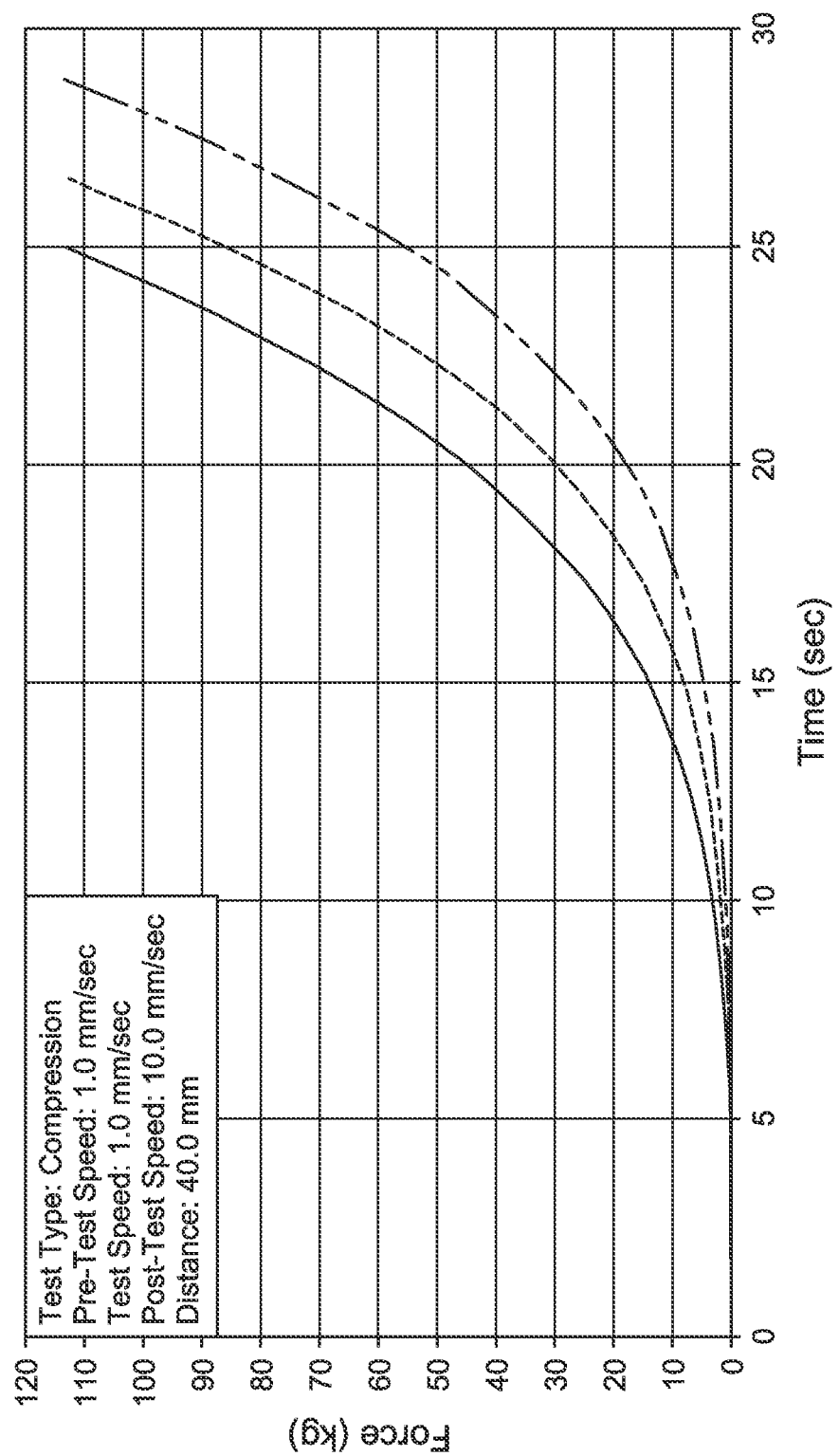
FIG. 8 is a graphic representation of the load-displacement curve generated from the compression data collected during the compression test of sample 5.
Figure 9:
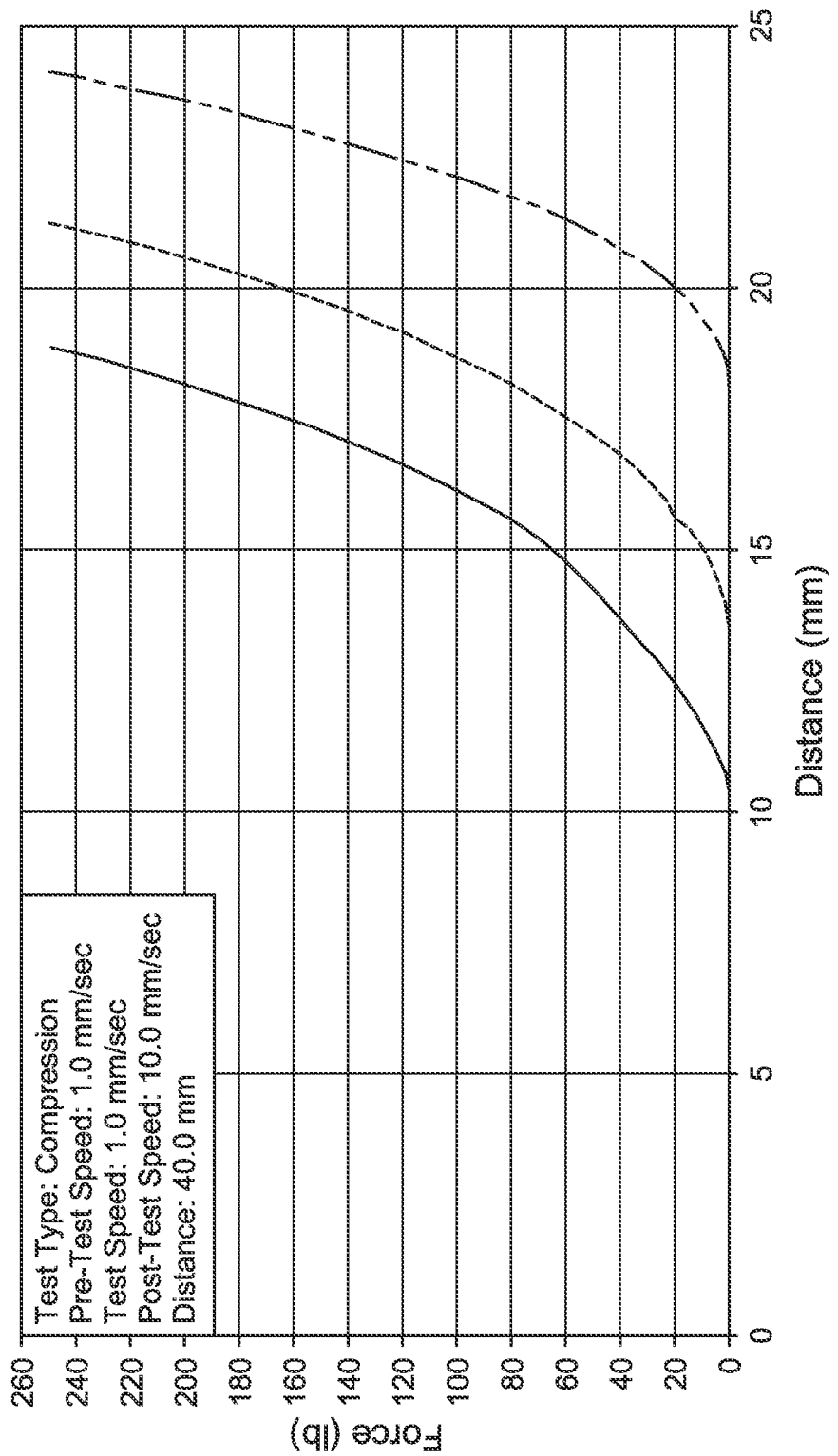
FIG. 9 is a graphic representation of the load-displacement curve generated from the compression data collected during the compression test of sample 6.

The rising flank of a load-displacement curve can be divided into three parts as shown in FIG. 3. The initial non-linear part 'A' of the rising flank is influenced by the initial foot embedment effect and also the uneven contact effect between the top of the gel and flat foot disc piston 30 at the beginning of the test. In other words, A represents the period when flat foot disc piston 30 moves to make full contact with the gel top of LCM test sample. As the gel top is not in proper contact with flat foot disc piston 30 to apply a full reactive force at the bottom of flat foot disc piston 30, the reaction force is non-linear. The slight embedment of flat foot disc piston 30 in the gel top of LCM test sample also plays a role in this non-linear response. This part of the initial rising flank of the curve is influenced by factors other than the gel matrix rigidity factor and is disregarded in determining the gel stiffness modulus.

The final non-linear part 'C' of the rising flank of the load-displacement curve is influenced by micro-scale failures of the gel matrix associated with particle rearrangement, particle reorientations, and particle readjustment under the increasing action of the compressive force. The micro-failures contribute to the non-linear behavior of part C. Therefore, this part of the rising flank is also influenced by factors other than the gel matrix rigidity factor and is excluded in determining the gel stiffness modulus.

The intermediate linear part 'B' of the rising flank of the load-displacement curve is not subject to the influences that effect A and C. Part B shows the reactive force response of LCM test sample after full contact between flat foot disc piston 30 and the gel top of the LCM test sample occurs. Therefore, the slope of the intermediate linear part of the load-displacement curve is used to determine gel stiffness modulus.

The load-displacement curve also provides information about the behavior of the LCM test sample following the initiation of extrusion flow, after the yield strength value is reached. For a deformation softening LCM, there will be a quick drop in the upward resistance due to increasing intensity of failure after the yield strength value is reached. For a constant deformation LCM, there will be no significant changes in the upward reactive force. For a deformation hardening LCM, the upward resistance will increase slightly before the LCM test sample is extruded.

EXAMPLES

Example 1

In example 1, six different gel-based LCMs (1-6) were produced. Although described with reference to gel-based LCM 1, the procedure for Example 1 was repeated for each of the six different gel-based LCMs. Gel-based LCM 1 was produced by mixing the components for gel-based LCM 1 with a high speed mixture for 10-15 minutes each. Gel-based LCM 1 was set aside for a cure time of 1-2 hours at room temperature and pressure. Without being bound to a specific theory, it is suspected that the cure time provides for inter-particle bonding, networking, and gelling and so the cure time enhances the gel properties of gel-based LCM 1.

After the cure time, test sample 1 from gel-based LCM 1 was collected. The size of test sample 1 was such that gel-based LCM 1 test sample 1 would fill the LCM test cell to the fill level of the cell space volume. The flat foot disc piston was placed on top of the gel-based LCM 1 test sample 1 so that the flat foot disc piston was flush with the cylinder wall. The normal stress applicator then applied a load through the load carrier arm and the piston rod to the flat foot disc piston so that the gel-based LCM 1 test sample 1 was subjected to a compression force at a constant displacement rate of 1 mm/sec. The acquisition system captured the compression data. Two additional test samples, test sample 2 and test sample 3 were collected from gel-based LCM 1 and the tests were repeated. The compression test data captured by the acquisition system produced the load versus displacement curves of FIGS. 4-9. The values for the gel stiffness modulus and yield strength, determined from the load-displacement curves, for each gel-based LCM test sample are in Table 1. "Lbf" is a unit of force known as the pound or pound-force.

TABLE 1

Experimentally Determined Gel Stiffness Modulus and Yield Strength

| Gel-Based LCM Systems | Gel Stiffness Modulus (lbf/mm) | Yield Strength (lbf) |
| --- | --- | --- |
| Gel-based LCM 1 - Test Sample 1 | 8.46 | 17.56 |
| Gel-based LCM 1 - Test Sample 2 | 11.63 | 16.50 |
| Gel-based LCM 1 - Test Sample 3 | 11.46 | 16.46 |
| Gel-based LCM 1 Average | 10.52 | 16.84 |
| Gel-based LCM 2 - Test Sample 1 | 28.60 | 94.26 |
| Gel-based LCM 2 - Test Sample 2 | 27.41 | 92.54 |
| Gel-based LCM 2 - Test Sample 3 | 21.93 | 90.19 |
| Gel-based LCM 2 Average | 25.98 | 92.33 |
| Gel-based LCM 3 - Test Sample 1 | 0.12 | 0.42 |
| Gel-based LCM 3 - Test Sample 2 | 0.11 | 0.43 |
| Gel-based LCM 3 - Test Sample 3 | 0.20 | 0.44 |
| Gel-based LCM 3 Average | 0.14 | 0.43 |
| Gel-based LCM 4 - Test Sample 1 | 0.21 | 0.50 |
| Gel-based LCM 4 - Test Sample 2 | 0.23 | 0.33 |
| Gel-based LCM 4 - Test Sample 3 | 0.23 | 0.61 |
| Gel-based LCM 4 Average | 0.19 | 0.42 |
| Gel-based LCM 5 - Test Sample 1 | 32.63 | >250 |
| Gel-based LCM 5 - Test Sample 2 | 32.83 | >250 |
| Gel-based LCM 5 - Test Sample 3 | 30.77 | >250 |
| Gel-based LCM 5 Average | 32.08 | >250 |
| Gel-based LCM 6 - Test Sample 1 | 71.02 | >250 |
| Gel-based LCM 6 - Test Sample 2 | 70.96 | >250 |
| Gel-based LCM 6 - Test Sample 3 | 74.67 | >250 |
| Gel-based LCM 6 Average | 72.22 | >250 |

According to the yield strength values in Table 1, gel-based LCM 1 has an average yield strength value of 16.84 lbf and an average gel stiffness modulus value of 10.52 lbf/mm. Gel-based LCM 2 has an average yield strength value of 92.33 lbf and an average gel stiffness modulus value of 25.98 lbf/mm. Based on these data points, gel-based LCM 2 will have higher flow resistance in larger fractures than gel-based LCM 1. Consequently, gel-based LCM 2 is more suitable for moderate to severe loss zones than gel-based LCM 1.

Gel-based LCM 3 and gel-based LCM 4 have very low average yield strength values, 0.43 lbf and 0.42 lbf, respectively, and gel stiffness modulus values, 0.14 lbf/mm and 0.19 lbf/mm, respectively. Due to strong flow dynamics in large fractures and vugular zones, LCMs with low yield strength and low gel stiffness modulus will not exhibit proper control of loss of circulation in moderate and severe loss zones alone without the aid of other loss circulation materials. These LCMs may exhibit successful control of loss of circulation in seepage loss zones and at the extreme low end of moderate loss zones Gel-based LCM 5 and gel-based LCM 6 have very high average yield strength values, >250 lbf, that were beyond the measurable range of the compression test rig. Additionally, these gel-based LCMs have higher gel stiffness modulus values compared to gel-based LCM 1 and gel-based LCM 2. The higher gel stiffness modulus values are consistent with the higher yield strength values of gel-based LCM 5 and gel-based LCM 6 over gel-based LCM 1 and gel-based LCM 2. Due to very high yield strength and gel stiffness modulus values, gel-based LCM 5 and gel-based LCM 6 are suitable for controlling for moderate and severe loss of circulation zones. Additional field test applications were run with gel-based LCM 5 in a loss of circulation zone. The field results of the application of the LCM 5 indicate much higher success rate compared to other LCM treatment jobs.

The scope of the present invention envisions and encompasses those embodiments that may suitably comprise, consist or consist essentially of the elements disclosed, and such embodiments may be practiced in the absence of an element not disclosed. For example, it can be recognized by those skilled in the art that certain steps can be combined into a single step.

Unless defined otherwise, all technical and scientific terms used have the same meaning as commonly understood by one of ordinary skill in the art to which this invention belongs.

The singular forms "a," "an," and "the" include plural referents, unless the context clearly dictates otherwise.

As used herein and in the appended claims, the words "comprise," "has," and "include" and all grammatical variations thereof are each intended to have an open, non-limiting meaning that does not exclude additional elements or steps.

"Optionally" means that the subsequently described event or circumstances may or may not occur. The description includes instances where the event or circumstance occurs and instances where it does not occur.

Ranges may be expressed herein as from about one particular value to about another particular value. When such a range is expressed, it is to be understood that another embodiment is from the one particular value to the other particular value, along with all combinations within said range.

Although the scope of the present invention has been described in detail, it should be understood that various changes, substitutions, and alterations can be made without departing from its principle and scope. Accordingly, the inventive scope should be determined by the appended claims and their appropriate legal equivalents.

What is claimed is:

1. A method for determining a mechanical characterization of a gel-based LCM using a compression test rig, the method comprising the steps of:
   placing a gel-based LCM sample volume in a cell space volume of a LCM test cell of the compression test rig, the compression test rig comprising:
      an LCM test cell, the LCM test cell configured to contain the gel-based LCM test sample, the LCM test cell comprising:
         a cylinder wall, the cylinder wall defining the cell space volume, wherein the cell space volume is configured to contain the gel-based LCM test sample, and
         a floor, the floor physically connected to the cylinder wall, the floor defining an extrusion hole, the extrusion hole having an extrusion hole diameter, the extrusion hole configured to extrude the gel-based LCM test sample to create an extruded gel, wherein the gel-based LCM sample volume fills the cell space volume to a fill level;
      an extruded gel collector, the extruded gel collector proximate to the floor of the LCM test cell, the extruded gel collector configured to receive the extruded gel from the extrusion hole as an extruded gel volume;
      a perforated disc, the perforated disc in contact with the floor of the LCM test cell and flush with the cylinder wall, the perforated disc comprising perforations, wherein the perforated disc is configured to allow the gel-based LCM test sample to pass through the perforations; and
      a flat foot disc piston, the flat foot disc piston in flush contact with the cylinder wall of the LCM test cell, the flat foot disc piston configured to compress the gel-based LCM test sample contained in the cell space volume at a displacement speed to produce compression data;
   placing the flat foot disc piston at the fill level in contact with the gel-based sample volume;
   applying a load to the flat foot disc piston to move the flat foot disc toward the floor of the LCM test cell at a displacement speed,
      wherein the flat foot disc compresses the gel-based LCM test sample contained in the cell space volume,
      wherein the gel-based LCM test sample is compressed to a compressed level,
      wherein a measured reactive force is produced in response to being compressed by the flat foot disc piston; and
   measuring compression data with an acquisition system, the acquisition system in electronic communication with the LCM test cell, the acquisition system configured to record the compression data, the acquisition system further configured to display the compression data.

2. The method of claim 1, further comprising the steps of:
   generating the load in a normal stress applicator, the normal stress applicator mechanically connected to a load cell carrier arm, the normal stress applicator configured to generate the load, wherein the load is operable to be variable in order to maintain a constant displacement speed;
   moving the load cell carrier arm, the load cell carrier arm mechanically connected to a piston rod, the load cell carrier arm configured to apply the load to the piston rod, the load cell carrier arm comprising a load cell, the load cell mechanically connected to the load carrier arm cell, the load cell configured to measure a measured reactive force of the gel-based LCM test sample, the load cell further configured to convert the measured reactive force into an electrical signal, wherein the electrical signal is recorded by the acquisition system, wherein the measured reactive force is produced in response to being compressed by the flat foot disc piston; and
   moving the piston rod, the piston road mechanically connected to the flat foot disc piston, the piston rod is configured to move the flat foot disc piston between the fill level and the compressed level.

3. The method of claim 1, the perforations comprising:
   a central perforation, the central perforation in the center of the perforated disc, the central perforation having a central perforation diameter; and
   a plurality of peripheral perforations, the plurality of peripheral perforations arranged in a ring around the central perforation to form a perforation ring, the perforation ring having a perforation ring diameter, the plurality of peripheral perforations having a peripheral perforation diameter.

4. The method of claim 1, wherein the extrusion hole diameter is 3.3 cm.

5. The method of claim 1, wherein the central perforation diameter is 3 mm.

6. The method of claim 1, wherein the peripheral perforation diameter is 3 mm.

7. The method of claim 1, wherein the perforation ring diameter is 2.6 cm.

8. The method of claim 1, wherein the mechanical characterization is selected from the group consisting of yield strength, gel stiffness modulus, and combinations thereof.

9. The method of claim 1, wherein the displacement speed is 1 mm/sec.

10. The method of claim 1, wherein the compression data is selected from the group consisting of time, the extruded gel volume, the load, the measured reactive force, the fill level, the compressed level, and combinations thereof.

11. A compression test rig apparatus for determining a mechanical characterization of a gel-based LCM test sample, the compression test rig apparatus comprising:
   an LCM test cell, the LCM test cell configured to contain the gel-based LCM test sample, the LCM test cell comprising:
      a cylinder wall, the cylinder wall defining a cell space volume, wherein the cell space volume is configured to hold the gel-based LCM test sample, and
      a floor, the floor being physically connected to the cylinder wall, the floor defining an extrusion hole, the extrusion hole having an extrusion hole diameter, the extrusion hole configured to extrude the gel-based LCM test sample to create an extruded gel;
   an extruded gel collector, the extruded gel collector being proximate to the floor of the LCM test cell, the extruded gel collector configured to receive the extruded gel from the extrusion hole as an extruded gel volume;
   a perforated disc, the perforated disc being in contact with the floor of the LCM test cell and flush with the cylinder wall, the perforated disc comprising perforations,
      wherein the perforated disc is configured to allow the gel-based LCM test sample to pass through the perforations; and a flat foot disc piston, the flat foot disc piston in flush contact with the cylinder wall of the LCM test cell, the flat foot disc piston configured to compress the gel-based LCM test sample contained in the cell space volume at a displacement speed to produce compression data.

12. The compression test rig apparatus of claim 11 further comprising:

an acquisition system, the acquisition system in electronic communication with the LCM test cell, the acquisition system configured to record the compression data, the acquisition system further configured to display the compression data.

13. The compression test rig apparatus of claim 11 further comprising:

a piston rod mechanically connected to the flat foot disc piston, configured to move the flat foot disc piston between a fill level and a compressed level;

a load cell carrier arm mechanically connected to the piston rod, the load cell carrier arm configured to apply a load to the piston rod, wherein the load is operable to be variable in order to maintain a constant displacement speed;

a load cell, the load cell mechanically connected to the load carrier arm, the load cell configured to measure a measured reactive force of the gel-based LCM test sample, the load cell further configured to convert the measured reactive force into an electrical signal, wherein the electrical signal is recorded by the acquisition system, wherein the measured reactive force is produced in response to being compressed by the flat foot disc piston; and a normal stress applicator, the normal stress applicator mechanically connected to the load cell carrier arm, the normal stress applicator configured to generate the load.

14. The compression test rig apparatus of claim 11, the perforations comprising:

a central perforation, the central perforation being in the center of the perforated disc, the central perforation having a central perforation diameter; and a plurality of peripheral perforations, the plurality of peripheral perforations arranged in a ring around the central perforation to form a perforation ring, the perforation ring having a perforation ring diameter, the plurality of peripheral perforations having a peripheral perforation diameter.

15. The compression test rig apparatus of claim 11, wherein the extrusion hole diameter is 3.3 cm.

16. The compression test rig apparatus of claim 11, wherein the central perforation diameter is 3 mm.

17. The compression test rig apparatus of claim 11, wherein the peripheral perforation diameter is 3 mm.

18. The compression test rig apparatus of claim 11, wherein the perforation ring diameter is 2.6 cm.

19. The compression test rig apparatus of claim 11, wherein the mechanical characterization is selected from the group consisting of yield strength, gel stiffness modulus, and combinations thereof.

20. The compression test rig apparatus of claim 11, wherein the displacement speed is 1 mm/sec.

21. The compression test rig apparatus of claim 11, wherein the compression data is selected from the group consisting of time, the extruded gel volume, the load, the measured reactive force, the fill level, the compressed level, and combinations thereof.

* * * * *